(12) United States Patent
Olivo et al.

(10) Patent No.: US 8,309,738 B2
(45) Date of Patent: Nov. 13, 2012

(54) METHODS FOR THE PREPARATION OF THIAZOLIDINETHIONE INDENE-BASED CHIRAL AUXILIARIES

(75) Inventors: Horacio F. Olivo, Iowa City, IA (US); Antonio Victor Osorio Lozada, Visp (CH)

(73) Assignee: University of Iowa Research Foundation, Iowa City, IA (US)

( * ) Notice: Subject to any disclaimer, the term of this patent is extended or adjusted under 35 U.S.C. 154(b) by 486 days.

(21) Appl. No.: 12/685,014

(22) Filed: Jan. 11, 2010

(65) Prior Publication Data

US 2010/0179330 A1  Jul. 15, 2010

Related U.S. Application Data

(60) Provisional application No. 61/144,138, filed on Jan. 12, 2009.

(51) Int. Cl.
  C07D 277/60  (2006.01)
  C07F 9/38    (2006.01)
  C07C 213/00  (2006.01)

(52) U.S. Cl. .......................... 548/150; 564/15
(58) Field of Classification Search ............ 548/150; 564/15, 428
  See application file for complete search history.

(56) References Cited

U.S. PATENT DOCUMENTS

| | | | |
|---|---|---|---|
| 1,597,089 A | 9/1924 | Rosenstein |
| 1,872,452 A | 8/1932 | Hirschkind |
| 2,011,302 A | 8/1935 | Rosentein |
| 2,037,717 A | 4/1936 | De Witt Graves |
| 2,037,718 A | 4/1936 | De Witt Graves |
| 3,607,865 A | 9/1971 | Dyer et al. |
| 5,194,619 A | 3/1993 | Reuschling et al. |

OTHER PUBLICATIONS

Arya and Qin, "Advance in Asymmetric Enolate Methodolgy," Tetrahedron 2000, 56, 917-947.
Evans et al, "Stereoselective Aldol Condensations," Top. Stereochem. 1982, 13, 1-115.
Ager et al., "1,2-Amino alcohols and Their Heterocyclic Derivatives as Chiral Auxiliaries in Asymmetric Synthesis," Chem. Rev. 1996, 96, 835-875.
Evans et al., "Erythro-Selective Chiral Aldol Condensations via Boron Enolates," J. Am. Chem. Soc. 1981, 103, 2127-2129.
Oppolzher et al., "Bornanesultam-Directed Asymmetric Synthesis of Crystalline, Enantiomerically Pure Syn Aldols," J. Am. Chem. Soc. 1990, 112, 2767-2772.
Sibi et al, "A New Chiral Oxadolidinone Derived From Diphenylalaninol. Aldol, Alkylation, and Diels-Alder Reactions," Tretrahedron Lett. 1995, 36,8965-8968.
Walker and Heathcock, "Extending the Scope of the Evans Asymmetric Aldol Reaction: Preparation of Anti and 'Non-Evans' Syn Aldols," J. Org. Chem. 1991, 56, 5747-5750.
Bonner and Thornton, "Asymmetric aldol Reactions. A New Camphor-Derived Chiral Auxiliary Giving Highly Stereoselective Aldol Reactions of both Lithium and Titanium (IV) Enolates," J. Am. Chem. Soc. 1991, 113, 1299-1308.
Yan et al., "Asymmetric Aldol Reactions: A Novel Model for Switching between Chelation and Non-Chelation-Controlled Aldol Reactions," J. Am. Chem. Soc. 1993, 115, 2613-2621.
Crimmins et al., "Asymmetric Aldol Additions with Titanium Enolates of Acyloxazolidinethiones: Dependence of Selectivity on Amine Base and Lewis Acid Stoichiometry," J. Am. Chem. Soc. 1997, 119, 7883-7884.
Crimmins et al., "Asymmetric Aldol Additions: Use of Titanium Tetrachloride and (-)-Sparteine for the Soft Enolization of N-Acyl Oxadolidinones, Oxazolidinethiones, and Thiazolidinethiones," J. Org. Chem. 2001, 66, 894-902.
Evans et al., "Diastereoselective Magnesium Halide-Catalyzed anti-Aldol Reactions fo Chiral N-Acyloxazolidinones," J. Am. Chem. Soc. 2002, 124, 392-393.
Evans et al., "Magnesium Halide-Catalyzed Anti-Aldol Reactions of Chiral Np-Acylthiazolidinethiones," Org. Lett. 2002, 4, 1127-1130.
Nerz-Stormes and Thornton, Apparent Chelation Control in Aldol Reactions of Chiral (MexCHO)3 Ti-EnolatesTetrahedron Lett. 1986, 27, 897-900.
Masamune et al., "Double Asymmetric Synthesis and a New Strategy for Stereochemical Control in Organic Synthesis," Angew. Chem., Int. Ed. 1985, 24, 1-30.
Braun, "Stereoselective Aldol Reactions with a-Unsubstituted Chiral Enolates,"Angew. Chem., Int. Ed. Eng. 1987, 26, 24-37.
Nagao et al., "Use of Chiral 1,3-Oxazolidine-2-thiones in the Diastereoselective Synthesis of Aldols,"J. Chem. Soc., Chem. Commun. 1985, 1418.
Nagao et al., "New C4-Chiral 1,3-Oxazolidine-2-thiones: Excellent Chiral Auxiliaries for Highly Diastereocontrolled Aldol-Type Reactions of Acetic Acid and aB-Unsaturated Aldehydes," J. Org. Chem. 1986, 51, 2391-2393.
Velasquez and Olivo, "The Application of Chiral Oxazolidinethiones and Thiazolidinethiones in Asymmetric Synthesis," Curr. Org. Chem. 2002, 6, 303-340.
Ortiz and Sansinenea, "The synthetic versatility of oxazolidinethiones," J. Sulfur Chem. 2007, 28, 109-147.

(Continued)

Primary Examiner — Jason M Nolan
(74) Attorney, Agent, or Firm — McDonnell Boehnen Hulbert & Berghoff LLP

(57) ABSTRACT

Methods for the preparation of indene-based thiazolidinethiones are provided comprising contacting 1-amino-2,3-dihydro-1H-inden-2-ol, or a substituted derivative thereof, with an acid under suitable reaction conditions to provide a first intermediate; and contacting the first intermediate with an alkali xanthate in the presence of an alkali hydroxide under suitable reaction conditions to provide a compound of formula (III),

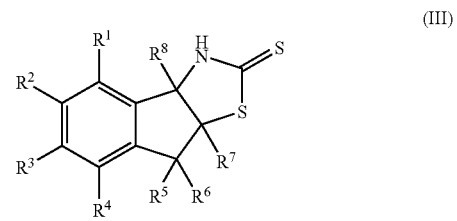

wherein $R^1$-$R^8$ are defined herein.

24 Claims, No Drawings

OTHER PUBLICATIONS

Yan et al., "Asymmetric aldol type Reactions of Acetate Imide Enolates," J. Org. Chem. 1995, 60, 3301-3306.

Gonzalez et al., "Asymmetric Acetate Aldol Reactions in Connection with an Enantioselective Total Synthesis of Macrolactin A," Tetrahedron Lett. 1996, 37, 8949-89-52.

Crimmins et al., "Total Synthesis of (+)-Laurencin: An Asymmetric Alkylation-Ring-Closing Metathesis Approach to Medium Ring Ethers," Org. Lett. 1999, 1, 2029-2032.

Romero-Ortega et al., "Synthesis of the C10-C17 fragment of aurisides and callipeltosides," Tetrahedron Lett. 2002, 43, 6439-6441.

Hodge and Olivo, "Stereoselective aldol additions of titanium enolates of N-acetyl-4-isopropyl-thiazolidinethione," Tetrahedron 2004, 60, 9397-9403.

Guz and Phillips, "Practical and Highly Selective Oxazolidinethione-Based Asymmetric Acetate Aldol Reactions with Aliphatic Aldehydes," Org. Lett. 2002, 4, 2253-2256.

Zhang et al., "Highly Selective Asymmetric Acetate Aldol Reactions of an N-Acetyl Thiazolidinethione Reagent," Org. Lett. 2004, 6, 23-25.

Zhang and Sammakia, "Synthesis of a New N-Acetyl Thiazolidinethione Reagent and It's Application to a Highly Selective Asymmetric Acetate Aldol Reaction," Org. Lett. 2004, 6, 3139-3141.

Crimmins and Shamszad, "Highly Selective Acetate Aldol Additions Using Mesityl-Substituted Chiral Auxiliaries," Org. Lett. 2007, 9, 149-152.

Ghosh et al., "Highly Enantioselective Aldol Reaction: Development of a New Chiral Auxiliary from cis-1-Amino-2-hydroxyindan," J. Chem. Soc., Chem. Commun. 1992, 1673-1674.

Pastor and Yus, "Asymmetric Ring Opening of Epoxides," curr. Org. Chem. 2005, 9, 1-29.

Delaunay et al., "Reactivity of B-Amino Alcohols with Carbon Disulfide, Study on the Synthesis of 2-Oxazolidinethiones and 2-Thiazolidinethiones," J. Org. Chem. 1995, 60, 6604-6607.

Kozhushkov et al., "Convenient and Inexpensive Synthesis of (IR,2R)-trans-1-Amino-6-nitroindan-2-ol," Adv. Synth. Catal. 2005, 347, 255-265.

Yamada et al., "Twisted Amides as Selective Acylating Agents for Hydroxyl Groups under Neutral Conditions: Models for Activated Peptides during Enzymatic Acyl Transfer Reaction," J. Org. Chem. 1996, 61, 5932-5938.

Dewey and Bafford, "The Reactions of B-Aminoalkyl Hydrogen Sulfates. II. The Reaction of Sodium B-Aminoalkyl SulfateDew Potassium Ethyl Xanthate," J. Org. Chem. 1965, 30, 495-500.

Andrade et al., "DCC/DMAP-Mediated Coupling of Carboxylic Acids with Oxazolidinones and Thiazolidinethiones," Synlett 2003, 15, 2351-2352.

Wu et al., "Removal of Thiazolidinethione Auxiliaries with Benzyl Alcohol Mediated by DMAP," J. Org. Chem. 2004, 69, 6141-6144.

Osorio-Lozada et al., "Synthesis and determination of the absolute stereochemistry of the enantiomers of adrafinil and modafinil," Tetrahedron: Asymm. 2004, 15, 3811-3815.

METHODS FOR THE PREPARATION OF THIAZOLIDINETHIONE INDENE-BASED CHIRAL AUXILIARIES

CROSS REFERENCE TO RELATED APPLICATIONS

This application claims the benefit of priority to U.S. Provisional Patent Application Ser. No. 61/144,138, filed Jan. 12, 2009, the disclosure of which is incorporated herein by reference.

STATEMENT OF GOVERNMENT INTEREST

The invention described herein was made in part with government support under grant number EEC-0310689 awarded by the National Science Foundation. The United States Government has certain rights in the invention.

FIELD OF THE INVENTION

The invention described herein describes methods of synthesis of thiazolidinethione thione chiral auxiliary compounds and intermediate compounds for preparation of the chiral auxiliaries.

BACKGROUND OF THE INVENTION

The asymmetric aldol addition mediated by a chiral auxiliary is one of the most commonly used reactions to form a carbon-carbon bond and two chiral carbons adjacent to a carbonyl group stereoselectively (see, Arya and Qin, *Tetrahedron* 2000, 56, 917-947; Evans et al., *Top. Stereochem.* 1982, 13, 1-115; Ager et al., *Chem. Rev.* 1996, 96, 835-875). Several methodologies and chiral auxiliaries have been developed for this endeavor; particularly dibutylboron enolates of N-acyloxazolidinones have been valuable to prepare the Evans syn-propionate aldol products (see, Evans et al., *J. Am. Chem. Soc.* 1981, 103, 2127-2129; Oppolzer et al., *J. Am. Chem. Soc.* 1990, 112, 2767-2772; and Sibi et al., *Tetrahedron Lett.* 1995, 36, 8965-8968). Utilizing the same chiral auxiliary, titanium(IV) enolates of N-acyloxazolidinones were shown to provide the non-Evans syn-propionate aldol products (see, Walker and Heathcock, *J. Org. Chem.* 1991, 56, 5747-5750; Bonner and Thornton, *J. Am. Chem. Soc.* 1991, 113, 1299-1308; and Yan et al., *J. Am. Chem. Soc.* 1993, 115, 2613-2621). Recent reports suggest that by using chlorotitanium(IV) enolates of N-propionate thiazolidinethiones we can access the Evans syn-aldol product when adding one equivalent of sparteine, and the non-Evans syn-aldol product when adding two equivalents of the same base (see, Crimmins et al., *J. Am. Chem. Soc.* 1997, 119, 7883-7884; and Crimmins et al., *J. Org. Chem.* 2001, 66, 894-902). This change in facial selectivity is the result of switching mechanistic pathways between chelated and non-chelated transition states. Evans reported the anti-aldol reaction promoted by catalytic amounts of magnesium halide in the presence of triethylamine and chlorotrimethylsilane. (see, Evans et al., *J. Am. Chem. Soc.* 2002, 124, 392-393; and Evans et al., *Org. Lett.* 2002, 4, 1127-1130). These conditions deliver the Evans anti-aldol product when using an oxazolidinone, and the opposite aldol product when using a thiazolidinethione.

Chiral auxiliary driven acetate-type aldol reactions have proven more difficult than the corresponding propionate reactions. N-Acetate oxazolidinones and other chiral auxiliaries did not provide the diastereoselectivities achieved with the corresponding N-propionates (see, Nerz-Stormes and Thornton, *Tetrahedron Lett.* 1986, 27, 897-900; Masamune et al., *Angew. Chem., Int. Ed.* 1985, 24, 1-XX; and Braun, *Angew. Chem., Int. Ed. Eng.* 1987, 26, 24-37). Several methods and strategies have been realized to solve this problem. Among them, Nagao's acetate aldol reaction with tin enolate of N-acetyl thiazolidinethione delivered high diastereoselectivities (see, Nagao et al., *J. Chem. Soc., Chem. Commun.* 1985, 1418; Nagao et al., *J. Org. Chem.* 1986, 51, 2391-2393; Velasquez and Olivo, *Curr. Org. Chem.* 2002, 6, 303-340; and Ortiz and Sansinenea, *J. Sulfur Chem.* 2007, 28, 109-147). However, the high price and irreproducibility of tin triflate prompted others to investigate other Lewis acids for this aldol reaction. The more economic titanium(IV) enolate was found to be highly efficient (see, Yan et al., *J. Org. Chem.* 1995, 60, 3301-3306; Gonzalez et al., *Tetrahedron Lett.* 1996, 37, 8949-8952; Crimmins et al., *Org. Lett.* 1999, 1, 2029-2032; Romero-Ortega et al., *Tetrahedron Lett.* 2002, 43, 6439-6441; and Hodge and Olivo, *Tetrahedron* 2004, 60, 9397-9403). More sterically encumbered thiazolidinethiones and oxazolidinethiones have also been prepared to deliver higher diastereoselectivities, albeit at a higher price for starting materials and or longer reaction sequences (see, Guz and Phillips, *Org. Lett.* 2002, 4, 2253-2256; Zhang et al., *Org. Lett.* 2004, 6, 23-25; Zhang and Sammakia, *Org. Lett.* 2004, 6, 3139-3141; and Crimmins and Shamszad, *Org. Lett.* 2007, 9, 149-152).

Therefore, there exists a need in the art to address the preceding shortcomings of the art, in particular with respect to the facile and lower-cost preparation of chiral auxiliaries which show diastereoselectivity when utilized as N-acetate enols.

SUMMARY OF THE INVENTION

In a first aspect, the invention provides methods for preparing a compound comprising
(A) contacting a compound of formula (I),

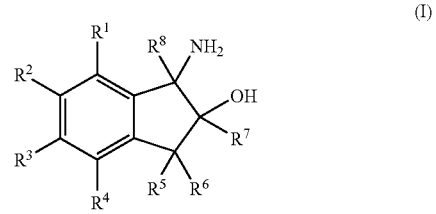

wherein
$R^1$-$R^6$ are each independently hydrogen, cyano, halo, nitro, $C_{1-6}$alkyl, $C_{2-6}$alkenyl, $C_{2-6}$alkynyl, $C_{3-8}$cycloalkyl, heterocyclyl, aryl, or heteroaryl, wherein the alkyl, alkenyl, alkynyl, cycloalkyl, heterocyclyl, aryl, and heteroaryl groups are each optionally substituted with one or more groups which are each independently cyano, halo, nitro, $C_{1-6}$alkyl, $C_{2-6}$alkenyl, $C_{2-6}$alkynyl, $C_{3-8}$cycloalkyl, heterocyclyl, aryl, or heteroaryl;
$R^7$ and $R^8$ are each independently hydrogen, $C_{1-6}$alkyl, or phenyl, wherein the alkyl and phenyl groups are each optionally substituted with one or more groups which are each independently halo or $C_{1-6}$alkyl;
or one or more of
(a) $R^1$ and $R^2$ taken together with the carbon atoms to which they are bonded;
(b) $R^2$ and $R^3$ taken together with the carbon atoms to which they are bonded;

(c) $R^3$ and $R^4$ taken together with the carbon atoms to which they are bonded; and
(d) $R^5$ and $R^6$ taken together with the carbon atoms to which they are bonded, form a fused $C_{3-8}$cycloalkyl, heterocyclyl, aryl, or heteroaryl ring wherein the fused ring is optionally substituted with one or more groups which are each independently halo or $C_{1-6}$alkyl;

with sulfuric acid, phosphoric acid, or trifluoromethylsulfonic acid, under suitable reaction conditions to provide a first intermediate; and (B) contacting the first intermediate with a compound of formula (II),

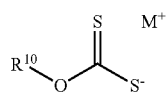
(II)

in the presence of an alkali hydroxide, wherein
$M^+$ is lithium, sodium, potassium, or ammonium; and
$R^{10}$ is $C_{1-20}$alkyl, $C_{2-20}$alkenyl, $C_{2-20}$alkynyl, $C_{3-8}$cycloalkyl$C_{1-6}$alkyl, heterocyclyl$C_{1-6}$alkyl, aryl$C_{1-6}$alkyl, heteroaryl$C_{1-6}$alkyl, $C_{3-8}$cycloalkyl, heterocyclyl, heteroaryl, or aryl, wherein
$R^{10}$ is optionally substituted with one or more groups which are each independently nitro, cyano, halo, hydroxy, $C_{1-6}$alkoxy, $C_{1-6}$alkyl, or $C_{1-6}$haloalkyl;
under suitable reaction conditions to provide a compound of formula (III),

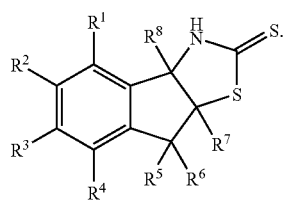
(III)

In a second aspect, the invention provides methods for preparing the first intermediate compound of the first aspect comprising contacting a compound of formula (I),

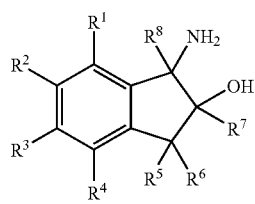
(I)

wherein
$R^1$-$R^6$ are each independently hydrogen, cyano, halo, nitro, $C_{1-6}$alkyl, $C_{2-6}$alkenyl, $C_{2-6}$alkynyl, $C_{3-8}$cycloalkyl, heterocyclyl, aryl, or heteroaryl, wherein the alkyl, alkenyl, alkynyl, cycloalkyl, heterocyclyl, aryl, and heteroaryl groups are each optionally substituted with one or more groups which are each independently cyano, halo, nitro, $C_{1-6}$alkyl, $C_{2-6}$alkenyl, $C_{2-6}$alkynyl, $C_{3-8}$cycloalkyl, heterocyclyl, aryl, or heteroaryl;

$R^7$ and $R^8$ are each independently hydrogen, $C_{1-6}$alkyl, or phenyl, wherein the alkyl and phenyl groups are each optionally substituted with one or more groups which are each independently halo or $C_{1-6}$alkyl;
or one or more of
(a) $R^1$ and $R^2$ taken together with the carbon atoms to which they are bonded;
(b) $R^2$ and $R^3$ taken together with the carbon atoms to which they are bonded;
(c) $R^3$ and $R^4$ taken together with the carbon atoms to which they are bonded; and
(d) $R^5$ and $R^6$ taken together with the carbon atoms to which they are bonded, form a fused $C_{3-8}$cycloalkyl, heterocyclyl, aryl, or heteroaryl ring wherein the fused ring is optionally substituted with one or more groups which are each independently halo or $C_{1-6}$alkyl;
with either
(i) sulfuric acid under suitable reaction conditions to provide a compound of the formula,

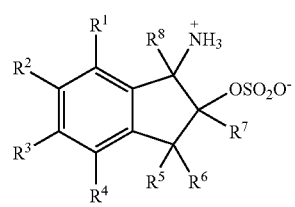
(VI)

(ii) trifluoromethylsulfonic acid under suitable reaction conditions to provide a compound of the formula,

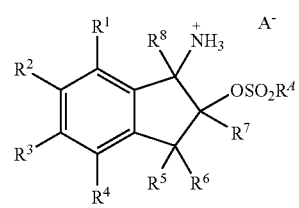
(V)

wherein $R^A$ is —$CF_3$ and $A^-$ is $R^ASO_2O^-$; or
(iii) phosphoric acid under suitable reaction conditions to provide a compound of the formula,

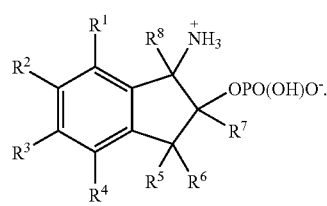
(VII)

DETAILED DESCRIPTION OF THE INVENTION

A novel indene-based thiazolidinethione analog of Ghosh's oxazolidinone (see, Ghosh et al., *J. Chem. Soc., Chem. Commun.* 1992, 1673-1674), has been prepared from commercially available trans-1-amino-2-indanol ((1R,2R)- trans-1-amino-2-indanol and (1S,2S)-trans-1-amino-2-indanol are available from Aldrich (Milwaukee, Wis.). Cat. Numbers: 663336 and 663344). The rigid nature of this chiral auxiliary promises to deliver high diastereoselectivities in aldol reactions and crystalline products.

The preparative methods provided herein for chiral auxiliary of formula (III) require no column chromatography purification, resulting in a more economic procedure by eliminating large amounts of solvents and expensive silica gel from the preparative processes. Further, the resulting thiazolidienthiones formed by the N-acylation of the auxiliaries of formula (III) as well as the aldol products resulting from such thiazolidienthions are generally solids, making their handling and purification more facile. In particular, the absolute stereochemistry of such aldol products can be readily determined by X-ray analysis due to the presence of heavy atoms (sulfur). In some embodiments, the starting materials of formula (I), such as non-racemic 1-amino-2-indanol, can be more economic than other starting materials for the preparation of Crimmins', Sammakia's, and Phillips-Sammakia's thiazolidinethiones.

In embodiments of the first aspect of the invention, the compound of formula (I) is of one of formulae (Ia)-(Ih),

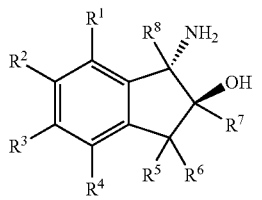
(Ia)

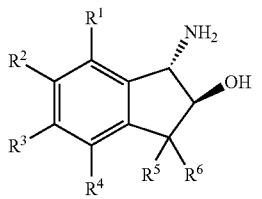
(Ib)

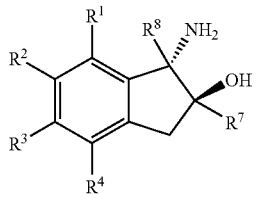
(Ic)

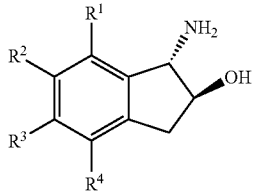
(Id)

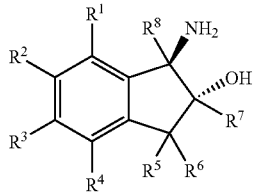
(Ie)

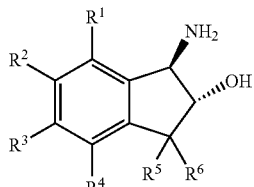
(If)

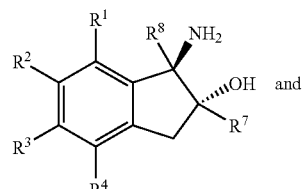
(Ig)

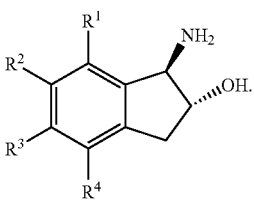
(Ih)

In embodiments, the compound of formula (I) is (1S,2S)-1-amino-2,3-dihydro-1H-inden-2-ol (Ii) or (1R,2R)-1-amino-2,3-dihydro-1H-inden-2-ol (Ij). In embodiments, the compound of formula (I) is (1R,2R)-1-amino-2,3-dihydro-1H-inden-2-ol (Ij). In embodiments, the compound of formula (I) is (1S,2S)-1-amino-2,3-dihydro-1H-inden-2-ol (Ii).

In some embodiment of any of the preceding embodiments, the acid is sulfuric acid. In other embodiments of any of the preceding embodiments, the acid is trifluoromethylsulfonic acid. In other embodiments of any of the preceding embodiments, the acid is phosphoric acid.

Suitable conditions for contacting the compound of any one of formulae (I) and (Ia)-(Ij) with an acid selected from sulfuric acid, phosphoric acid, and trifluoromethylsulfonic acid, include providing about 1-100 molar equivalents of the acid with respect to the compound of any one of formulae (I) and (Ia)-(Ij) and contacting the compounds at a temperature between about −40° C. and 40° C. For example, about 5 and 50 molar equivalents, or about 5 and 25 molar equivalents, or about 5 and 15 molar equivalents of the acid can be provided with respect to the compound of any one of formulae (I) and (Ia)-(Ij). Further, the contacting can take place at a temperature between about −30° C. and 30° C.; or about −20° C. and 30° C.; or about −10° C. and 30° C.; or about −10° C. and 20° C.; or about −10° C. and 10° C.

In embodiments of any one of formula (I) and (Ia)-(Ij), $R^{10}$ is $C_1$-$C_{20}$ alkyl or phenyl, wherein $R^{10}$ is optionally substituted with one or more groups which are each independently nitro, cyano, halo, hydroxy, $C_{1-6}$alkoxy, $C_{1-6}$alkyl, or $C_{1-6}$haloalkyl. In embodiments, $R^{10}$ is $C_{1-20}$ alkyl. In some embodiments, $R^{10}$ is $C_{1-4}$ alkyl or $C_{1-2}$ alkyl (e.g., ethyl).

In embodiments of any one of formula (I) and (Ia)-(Ij), $R^{10}$ is phenyl optionally substituted with one or more groups which are each independently nitro, cyano, halo, hydroxy, $C_{1-6}$alkoxy, $C_{1-6}$alkyl, or $C_{1-6}$haloalkyl.

In any of the preceding embodiments, the alkali hydroxide can be sodium or potassium hydroxide. Further, in any of the preceding embodiments, $M^+$ can be sodium or potassium; in some embodiments, $M^+$ is potassium.

Suitable conditions for contacting the first intermediate with a compound of formula (II), in the presence of an alkali hydroxide include providing about 1-5 molar equivalents of the compound of formula (II) with respect the first intermediate and contacting the same at a temperature between about room temperature (~25° C.) and about 100° C. For example, about 2-4 molar equivalents or about 2.5-3.5 molar equivalents of the compound of formula (II) with respect the first intermediate can be provided. Further, the contacting can occur at a temperature between about 30° C. and 90° C.; or about 40° C. and 90° C.; or about 50° C. and 90° C.; or about 50° C. and 80° C.; or about 60° C. and 80° C. Such contacting can take place using an aqueous solvent, such as aqueous acetonitrile, dimethylformamide, dimethylsulfoxide, dimethylacetamide, dioxane, tetrahydrofuran, diglyme, dimethoxyethane, acetone, methanol, ethanol, isopropanol, and mixtures thereof. Alternatively, such contacting can take place in solvent consisting essentially of water.

In embodiments of the first aspect of the invention, the compound of formula (III) is of one of formulae (IIIa)-(IIIh),

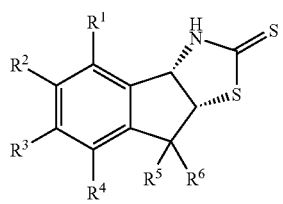 (IIIa)

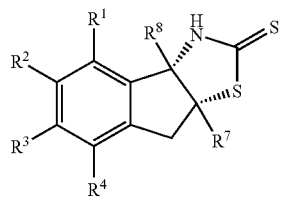 (IIIb)

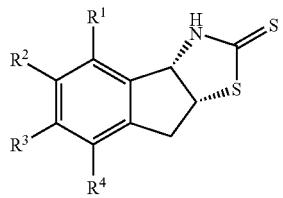 (IIIc)

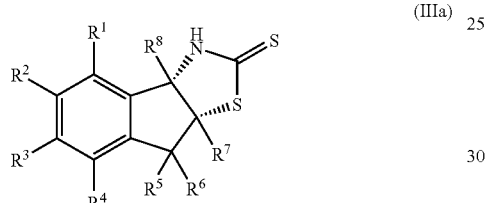 (IIId)

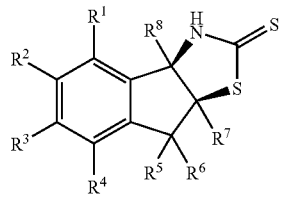 (IIIe)

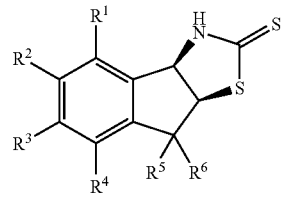 (IIIf)

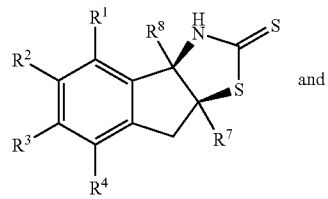 (IIIg) and

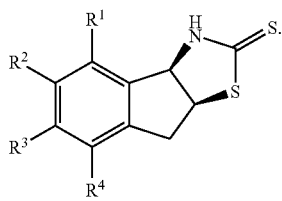 (IIIh).

In embodiments of the first aspect of the invention, the compound of formula (III) is (3aR,8aS)-3,3a,8,8a-tetrahydro-2H-indeno[1,2-d]thiazole-2-thione (IIIi) or (3aS,8aR)-3,3a,8,8a-tetrahydro-2H-indeno[1,2-d]thiazole-2-thione (IIIj). In embodiments, the compound of formula (III) is (3aR,8aS)-3,3a,8,8a-tetrahydro-2H-indeno[1,2-d]thiazole-2-thione (IIIi). In other embodiments, the compound of formula (III) is (3aS,8aR)-3,3a,8,8a-tetrahydro-2H-indeno[1,2-d]thiazole-2-thione (IIIj).

In embodiments of any of the preceding, the method further comprises contacting the compound of any one of formulae (III) and (IIIa)-(IIIj) with (a) a compound of the formula $R^N$—X or $R^N$—O—$R^N$, wherein X is halo, and each $R^N$ is independently C(O)CH($R^{21}$)$R^{20}$ or C(O)C($R^{21}$)=CH($R^{20}$), wherein $R^{20}$ is hydrogen, $C_{1-6}$alkyl, $C_{2-6}$alkenyl, $C_{2-6}$alkynyl, aryl$C_{1-6}$alkyl, aryl$C_{2-6}$alkenyl, heteroaryl$C_{1-6}$alkyl, heteroaryl$C_{2-6}$alkenyl, $C_{3-8}$cycloalkyl$C_{1-6}$alkyl, $C_{3-8}$cycloalkyl$C_{1-6}$alkenyl, heterocyclyl$C_{1-6}$alkyl, heterocyclyl$C_{2-6}$alkenyl, aryl, heteroaryl, $C_{3-8}$cycloalkyl, or heterocyclyl; and $R^{21}$ is hydrogen or $C_{1-6}$alkyl;

(b) a compound of the formula $R^N$—OH in the presence of an amide coupling reagent, under suitable reaction conditions to provide a compound of formula (IV),

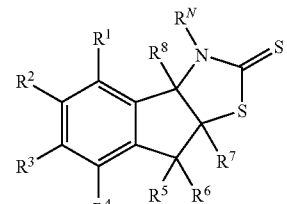 (IV)

In embodiments, the compound of formula (IV) is of one of formulae (IVa)-(IVh), (IVa) 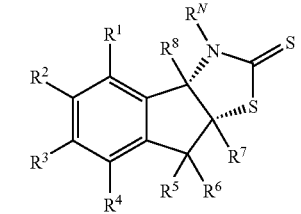

(IVb) 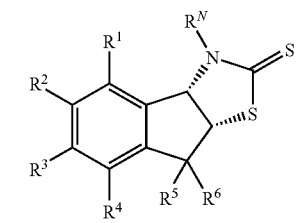

(IVc) 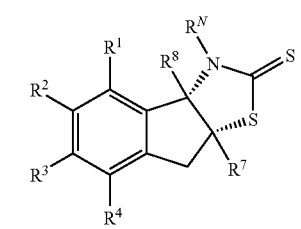

(IVd) 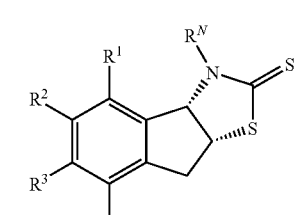

(IVe) 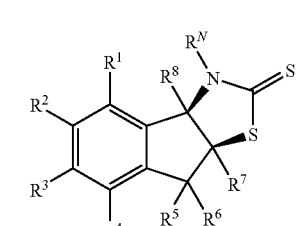

(IVf) 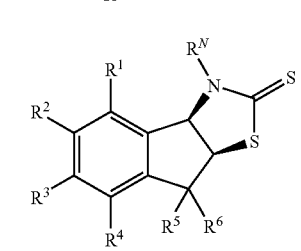

(IVg) 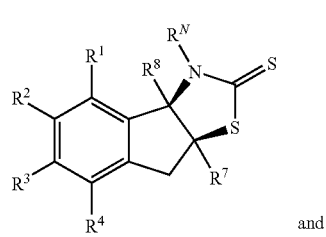

and

-continued (IVh) 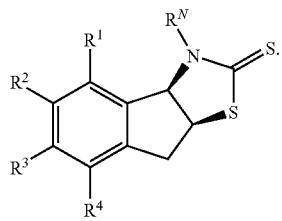

In embodiments, the compound of formula (IV) is 1-((3aS,8aR)-2-thioxo-2H-indeno[1,2-d]thiazol-3 (3 aH,8H,8aH)-yl)ethanone (IVi); 1-((3aS,8aR)-2-thioxo-2H-indeno[1,2-d]thiazol-3(3aH,8H,8aH)-yl)propan-1-one (IVj); 1-((3aR,8aS)-2-thioxo-2H-indeno[1,2-d]thiazol-3(3aH,8H,8aH)-yl)propan-1-one (IVk); or 1-((3aR,8aS)-2-thioxo-2H-indeno[1,2-d]thiazol-3(3aH,8H,8aH)-yl)ethanone (IVl).

In embodiments of any one of formulae (IV) and (IVa)-(IVl), $R^N$ is —C(O)CH($R^{21}$)$R^{20}$. In embodiments of any one of formulae (IV) and (IVa)-(IVl), $R^N$ is —C(O)C($R^{21}$)=CH($R^{20}$).

In embodiments of any one of formulae (IV) and (IVa)-(IVl), $R^N$ is —C(O)$C_{1-6}$alkyl or —C(O)C($R^{21}$)=CH($R^{20}$), wherein $R^{20}$ and $R^{21}$ are independently hydrogen or $C_{1-6}$alkyl. In embodiments of any one of formulae (IV) and (IVa)-(IVl), $R^N$ is —C(O)$C_{1-6}$alkyl. For example, $R^N$ is —C(O)$CH_3$ or —C(O)$CH_2CH_3$. In some embodiments, $R^N$ is —C(O)$CH_3$. In some embodiments, $R^N$ is —C(O)$CH_2CH_3$. In some embodiments, $R^N$ is —C(O)C($CH_3$)=CH($CH_3$), —C(O)C(H)=CH($CH_3$), or —C(O)C(H)=$CH_2$.

In the preceding methods, the compounds of any one of formulae (III) and (IIIa)-(IIIj) can be contacted with a compound of the formula $R^N$—X (e.g., wherein X is chloro or bromo) to provide the compounds of formula (IV). The compounds of any one of formulae (III) and (IIIa)-(IIIj) can be also contacted with a compound of the formula $R^N$—O—$R^N$ to provide the compounds of formula (IV).

Suitable conditions for contacting the compound of any one of formulae (III) and (IIIa)-(IIIj) with a compound of the formula $R^N$—X or $R^N$—O—$R^N$, include providing about 0.5 to 10 equivalents of $R^N$—X or $R^N$—O—$R^N$ with respect to the compound of any one of formulae (III) and (IIIa)-(IIIj), where the contacting can occur at a temperature between about −80° C. and 100° C. For example, about 0.75 and 5 molar equivalents, or about 0.80 and 3 molar equivalents, or about 0.95 and 2 molar equivalents of $R^N$—X or $R^N$—O—$R^N$ can be provided with respect to the compound of any one of formulae (III) and (IIIa)-(IIIj). Further, the contacting can take place at a temperature between about −80° C. and 80° C.; or about −80° C. and 60° C.; or about −80° C. and 40° C.; or about −60° C. and 40° C.; or about −40° C. and 40° C.; or about −40° C. and 10° C. Optionally, between about 1 and 10 equivalents of a non-nucleophilic amine, such as triethylamine, N,N-diisopropylethylamine, 2,2,6,6-tetramethylpiperidine, pyridine, 2,6-lutidine, 4-dimethylaminopyridine, and N-methylmorpholine may be provided along with or prior to the addition of $R^N$—X or $R^N$—O—$R^N$.

Alternatively, the compounds of any one of formulae (III) and (IIIa)-(IIIj) can be contacted with a compound of the formula $R^N$—OH and an amide coupling agent to provide the compounds of formula (IV). Suitable amide coupling agents include carbodiimides, N,N'-carbonyldiimizadoles, or benzotriazol-1-yloxyphosphonium salts. For example, suitable carbodiimides include but are not limited to, 1,3-dicyclohexylcarbodiimide (DCC), 1,3-diisopropylcarbodiimide (DIC), 4-(2-{[(cyclohexylimino)methylene]amino}ethyl)-4-methylmorpholin-4-ium p-toluenesulfonate 1,3-di-tert-butylcarbodiimide, 1-(3-dimethylaminopropyl)-3-ethylcarbodiimide hydrochloride (EDC), 1,3-Di-p-tolylcarbodiimide, 1-tert-Butyl-3-ethylcarbodiimide, and 1,3-Bis(2,2-dimethyl-1,3-dioxolan-4-ylmethyl)carbodiimide.

N,N'-carbonyldiimizadoles include, but are not limited to, 1,1'-carbonyldiimidazole (CDI), and 1,1'-carbonylbis(2-methylimidazole).

Benzotriazol-1-yloxy salts include, but are not limited to, N-[(dimethylamino)(3H-[1,2,3]triazolo[4,5-b]pyridin-3-yloxy)methylene]-N-methylmethanaminium, benzotriazol-1-yloxytris(dimethylamino)phosphonium hexafluorophosphate (BOP), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), O-benzotriazol-1-yl-N,N,N',N'-tetramethyluronium tetrafluoroborate (TBTU), (2-(6-chloro-1H-benzotriazole-1-yl)-1,1,3,3-tetramethylaminium hexafluorophosphate) (HCTU), 1-H-benzotriazolium-1-[bis(dimethylamino)methylene]-5-chloro-3-oxide tetrafluoroborate (TCTU), benzotriazol-1-yl-oxy-tris-pyrrolidino-phosphoniumhexafluorophosphate (PyBOP).

Other suitable amide coupling agents include, but are not limited to, N-hydroxysuccinimide, 4-nitrophenol, 2-nitrophenol, bis(2-oxo-3-oxazolidinyl)phosphinic chloride (BOPCl), 1-Hydroxy-7-azabenzotriazole (HOAT), 1-hydroxybenzotriazole hydrate (HOBT), 1-hydroxy-6-chlorobenzotriazole, 3-hydroxy-1,2,3-benzotriazin-4(3H)-one (HOOBT), 3-(Diethoxyphosphoryloxy)-1,2,3-benzotriazin-4(3H)-one (DEPBT), and bromo-tris-pyrrolidino-phosphonium hexafluorophosphate (PyBrop). Such coupling agents can be utilized in the presence of a non-nucleophilic amine, such as triethylamine, N,N-diisopropylethylamine, 2,2,6,6-tetramethylpiperidine, pyridine, 2,6-lutidine, 4-dimethylaminopyridine, and N-methylmorpholine.

Suitable conditions for contacting the compound of any one of formulae (III) and (IIIa)-(IIIj) with a compound of the formula $R^N$—OH in the presence of an amide coupling reagent, include a providing about 0.5-5 molar equivalents of $R^N$—OH with respect to the compound of any one of formulae (III) and (IIIa)-(IIIj) and contacting the compounds at a temperature between about −80° C. and 150° C. For example, about 0.75 and 2 molar equivalents, or about 0.80 and 2 molar equivalents, or about 0.95 and 2 molar equivalents of $R^N$—OH can be provided with respect to the compound of any one of formulae (III) and (IIIa)-(IIIj). Further, the contacting can take place at a temperature between about −80° C. and 100° C.; or about −80° C. and 80° C.; or about −80° C. and 60° C.; or about −80° C. and 40° C.; or about −60° C. and 40° C.; or about −40° C. and 40° C.; or about −40° C. and 10° C. In some embodiments, between about 1 and 3 equivalents of the amide coupling agent can be provided. Optionally, between about 1 and 10 equivalents of a non-nucleophilic amine, such as triethylamine, N,N-diisopropylethylamine, 2,2,6,6-tetramethylpiperidine, pyridine, 2,6-lutidine, 4-dimethylaminopyridine, and N-methylmorpholine may be additionally provided.

The second aspect the invention provides methods for preparing the first intermediate compounds comprising contacting a compound of any one of formulae (I) and (Ia)-(Ij) (including any embodiments thereof, each as defined above), with
(i) sulfuric acid under suitable reaction conditions to provide a compound of the formula,

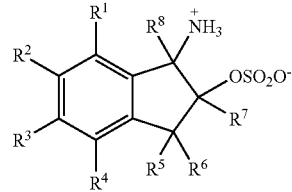

(ii) trifluoromethylsulfonic acid under suitable reaction conditions to provide a compound of the formula,

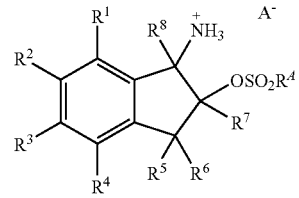

wherein $R^A$ is —$CF_3$ and $A^-$ is $R^A SO_2 O^-$; or (iii) phosphoric acid under suitable reaction conditions to provide a compound of the formula,

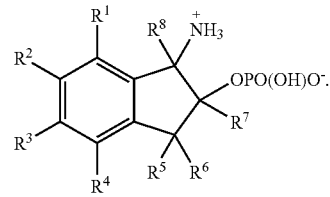

Suitable conditions for contacting the compound of any one of formulae (I) and (Ia)-(Ij) with an acid selected from sulfuric acid, phosphoric acid, and trifluoromethylsulfonic acid, include a providing about 1-100 molar equivalents of the acid with respect to the compound of any one of formulae (I) and (Ia)-(Ij) and contacting the compounds at a temperature between about −40° C. and 40° C. For example, about 5 and 50 molar equivalents, or about 5 and 25 molar equivalents, or about 5 and 15 molar equivalents of the acid can be provided with respect to the compound of any one of formulae (I) and (Ia)-(Ij). Further, the contacting can take place at a temperature between about −30° C. and 30° C.; or about −20° C. and 30° C.; or about −10° C. and 30° C.; or about −10° C. and 20° C.; or about −10° C. and 10° C.

Alkali metal xanthates, such as those of formula (II) in the preceding description of the invention, can be prepared as are known to those skilled in the art. For example, methods for making xanthates can be found in U.S. Pat. Nos. 1,507,089; 1,872,452; 2,011,302; 2,037,717; 2,037,718; and 3,607,865, each of which are hereby incorporated by references in their entirety.

Further, the 1-amino-2-indanols of formula (I) in the preceding description of the invention, can be prepared, for example, starting with a 1,4-butanedione with a cyclopentadiene to yield a substituted indene as described in U.S. Pat. No. 5,194,619 which is hereby incorporated by reference in its entirety. The substituted indene may then be converted by epoxidation (e.g., with MCPBA) followed by nucleophilic ring-opening according to methods known to those skilled in the art (e.g., see, Pator and Yus, *Curr. Org. Chem.* 2005, 9, 1-29, which is hereby incorporated by reference in its entirety) to yield the trans-1-amino-2-indanols for use in the present methods.

Definitions

All patents, patent applications, and literature references cited in the specification are herein incorporated by reference in their entirety. In the case of inconsistencies, the present disclosure, including definitions, will prevail.

The term "alkenyl" as used herein, means a straight or branched chain hydrocarbon containing from 2 to 20 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl or a bicyclic aryl or a tricyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, azulenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to dihydroanthracenyl, fluorenyl, and tetrahydrophenanthrenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cycloalkyl" as used herein, means a monocyclic, bicyclic, or tricyclic ring system. Monocyclic ring systems are exemplified by a saturated cyclic hydrocarbon group containing from 3 to 10 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle, or a bicyclic heterocycle fused to a monocyclic heteroaryl. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9, 9a-hexahydrodibenzo[b,d]thienyl.

The term "heterocyclylalkyl" as used herein, means a heterocycle, as defined herein, appended to the parent molecular moiety through an alkyl group, as defined herein.

The term "nitro" as used herein, means a —NO$_2$ group.

EXAMPLES

All moisture-sensitive reactions were carried out in oven-dried glassware under argon atmosphere. Melting point (m.p.) measurements are uncorrected and were determined on a Thomas-Fisher capillary melting point apparatus. Optical rotations were measured in a JASCO P-1020 polarimeter with sodium D-line (589 nm) and are reported on a concentration (c) of grams/100 mL of solvent. Nuclear Magnetic Resonance (NMR) spectra were measured at 300 MHz on a Bruker™ Avance 300. $^1$H NMR chemical shifts ($\delta$) are reported in parts per million (ppm) relative to Me$_4$Si ($\delta$=0.0 ppm) with coupling constants (J) reported in Hertz (Hz). Multiplicities are reported as singlet (s), doublet (d), triplet (t), quartet (q), multiplet (m), broad singlet (bs). $^{13}$C NMR are reported using 77.2 ppm (CDCl$_3$), and 39.5 ppm (DMSO-d$_6$) as internal references. Carbon signal multiplicities were determined by DEPT. High resolution mass spectra were performed at either the University of Iowa Mass Spectrometry Facility or at Amgen, Thousand Oaks, Calif.

Example 1

Preparation of Thiazolidinethione Via Standard Methods

A general procedure for the synthesis of chiral oxazolidinethiones and thiazolidinethiones is to treat 1,2-aminols derived from alpha-aminoacids with carbon disulfide and base (see, Delaunay et al., *J. Org. Chem.* 1995, 60, 6604-6607). Oxazolidinethiones are obtained preferentially when a mild base is employed, and thiazolidinethiones can be prepared in excellent yields when a stronger base is used instead. However, when this latter method was applied to trans-amino-2-indanol 1 (see, Kozhushkov et al., *Adv. Synth. Catal.* 2005, 347, 255-265), thiazolidinethione 2 was obtained in poor yield.

Example 2

Preparation of Thiazolidinethiones

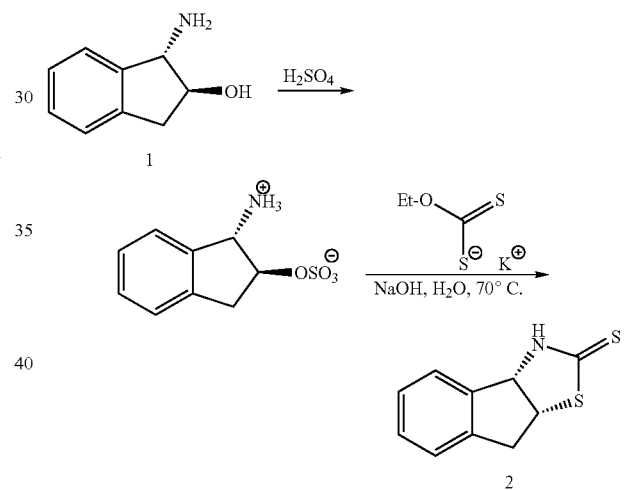

We have unexpectedly found that thiazolidinethiones can be obtained in very good yield when a trans-aminoindanol is first treated with sulfuric acid, and then the crude sulfated indanol was treated with an alkali alkyl xanthate and aqueous sodium hydroxide and the mixture heated to 75° C. for 16 h. (see, Yamada et al., *J. Org. Chem.* 1996, 61, 5932-5938; and Dewey and Bafford, *J. Org. Chem.* 1965, 30, 495-500). Using the following protocol, a single purification step, by column chromatography, was utilized to obtain clean thiazolidinethione 2.

(4S,5R)-Indano[1,2-d]thiazolidin-2-thione (2). Well stirred conc. sulfuric acid (28 mL, 506 mmol) cooled to 0° C. was treated with small portions of (1S,2S)-trans-1-amino-2-indanol (1, 5.96 g, 40 mmol) over 20 minutes. The reaction mixture was stirred 20 minutes further after the addition of the last portion of the amino-indanol. The light-brown clear viscous reaction mixture was poured over crushed ice (approx. 100 g). The precipitate was collected by filtration and the solids were washed with ice-cold H$_2$O (20 mL).

Sulfuric Acid Mono-(trans-1-amino-indan-2-yl) Ester: White solid, silica gel TLC R$_f$ 0.39 (7:3 CHCl$_3$-MeOH);

m.p.=product decomposed without melting; $^1$H NMR (DMSO-$d_6$) δ 8.47 (2H, bs), 7.51 (1H, m), 7.33 (3H, m), 4.92 (1H, dd, J=13.0, 7.0 Hz), 4.72 (1H, m), 3.35 (1H, dd, J=16.4, 6.8 Hz), 2.98 (1H, dd, J=16.4, 7.6 Hz); $^{13}$C NMR (DMSO-$d_6$) δ 139.8 (C), 136.4 (C), 129.3 (CH), 127.2 (CH), 125.0 (CH), 124.4 (CH), 79.2 (CH), 59.9 (CH), 36.6 (CH$_2$). The white solid (ammonium sulfate salt) was transferred into a 500-mL round-bottom reaction flask. Potassium ethyl xanthate (19.25 g, 120 mmol, 3 eq.) was added to the solid followed by addition of a 0.5 N solution of sodium hydroxide (80 mL, 1.86 g of NaOH, 40 mmol). A reflux condenser was connected to the reaction flask and the reaction mixture was stirred at 70° C. overnight. The reaction mixture was allowed to cool down and extracted with CH$_2$Cl$_2$ (4×50 mL). The combined organic phases were dried over anhydrous Na$_2$SO$_4$ and the solvent evaporated giving a light yellow solid: 7.5 g (92% yield). For analytical purposes a portion of the crude was purified by silica gel column chromatography and eluted with petroleum ether-ethyl acetate (7:3) affording thiazolidinethione chiral auxiliary 2 as white solid powder. Silica gel TLC $R_f$ 0.34 (7:3, petroleum ether-ethyl acetate), m.p.=185-186° C.; $[α]_{D25}$=+52.3 (c 1.0, CHCl$_3$); $^1$H NMR (CDCl$_3$) δ 8.69-8.49 (1H, bs), 7.34 (4H, m), 5.61 (1H, d, J=8.3 Hz), 4.80 (1H, ddd, J=8.3, 7.6, 3.3 Hz), 3.50 (1H, dd, J=17.1, 7.6 Hz), 3.28 (1H, dd, J=17.1, 3.3 Hz); $^{13}$C NMR (CDCl$_3$) δ 200.1 (CS), 140.3 (C), 138.3 (C), 129.8 (CH), 128.2 (CH), 125.5 (CH), 124.9 (CH), 72.9 (CH), 51.9 (CH), 40.0 (CH$_2$). HRMS (MALDI-TOF) calculated for (C$_{10}$H$_9$NS$_2$+H) m/z 208.0255, found m/z 208.0267.

Example 3

N-Acylation

Acylation of the was accomplished in very good yields by treating the thiazolidinethione with the corresponding acyl chloride or by coupling with the carboxylic acid (see, Andrade et al., Synlett 2003, 15, 2351-2352).

3-((4S,5R)-indano[1,2-d]thiazolidin-2-thione)-ethan-1-one (3). Acetyl chloride (1.17 g, 1.1 mL, 15 mmol) was added dropwise to a stirred solution of thiazolidinethione 2 (2.07 g, 10 mmol), and triethylamine (2.02 g, 2.78 mL, 20 mmol) in dichloromethane (80 mL) under argon atmosphere at room temperature. After the addition, the reaction mixture was stirred at room temperature overnight. The reaction mixture was diluted with CH$_2$Cl$_2$ (40 mL) and washed with H$_2$O (3×30 mL). The organic phase was dried over anhydrous Na$_2$SO$_4$ and evaporated to give a light-brown oil. The residue was purified by silica gel flash column chromatography (3×10 cm). Elution with petroleum ether-ethyl acetate (8:2) delivered a yellow solid: 2.45 g (98% yield). Silica gel TLC $R_f$ 0.32 (8:2, petroleum ether-ethyl acetate); m.p.=150-151° C.; $[α]_{D25}$=+646.3 (c 1.0, CHCl$_3$); $^1$H NMR (CDCl$_3$) δ 7.41-7.28 (4H, m), 6.60 (1H, d, J=7.1 Hz), 4.57 (1H, dd, J=7.1, 6.1 Hz), 3.38 (1H, dd, J=17.0, 6.1 Hz), 3.15 (1H, d, J=17.0 Hz), 2.86 (3H, s); $^{13}$C NMR (CDCl$_3$) δ 201.6 (CS), 171.8 (CO), 139.1 (C), 138.9 (C), 129.6 (CH), 128.2 (CH), 126.0 (CH), 125.3 (CH), 75.5 (CH), 46.9 (CH), 36.3 (CH$_2$), 27.0 (CH$_3$). HRMS (EI) calculated form (C$_{12}$H$_{11}$NOS$_2$) m/z 249.0282, found m/z 249.0280.

3-((4S,5R)-indano[1,2-d]thiazolidin-2-thione)-propan-1-one (4). Propionyl chloride (416 mg, 0.4 mL, 4.5 mmol) was added dropwise to a stirred solution of thiazolidinethione 2 (609 mg, 3 mmol), and triethylamine (670 mg, 0.84 mL, 6 mmol) in dichloromethane (20 mL) in an argon atmosphere at room temperature. The reaction mixture, which gradually became yellow, was stirred at room temperature for 3 hours. The reaction mixture was diluted with CH$_2$Cl$_2$ (50 mL). The organic layer was collected and washed with H$_2$O (2×50 mL). The organic layer was dried over anhydrous Na$_2$SO$_4$ and evaporated to give a brown-yellow solid. The crude residue was purified by silica gel flash column chromatography on a silica gel column (3 cm×10 cm). Elution with petroleum ether-ethyl acetate (85:15) afforded a yellow solid: 2.37 g (90% yield). Silica gel TLC $R_f$ 0.30 (85:15, petroleum ether-ethyl acetate); m.p.=134-135° C.; $[α]_{D25}$=+660.6 (c 1.0, CHCl$_3$); $^1$H NMR (CDCl$_3$) δ 7.37-7.25 (4H, m), 6.56 (1H, d, J=7.1 Hz), 4.52 (1H, dd, J=7.1, 6.0 Hz), 3.43 (1H, dq, J=17.7, 7.2 Hz), 3.35 (1H, dd, J=17.0, 6.0 Hz), 3.15 (1H, dq, J=17.7, 7.2 Hz), 3.10 (1H, d, J=17.0 Hz), 1.24 (3H, t, J=7.2 Hz); $^{13}$C NMR (CDCl$_3$) δ 201.1 (CS), 175.9 (CO), 139.1 (C), 138.9 (C), 129.5 (CH), 128.2 (CH), 125.9 (CH), 125.2 (CH), 75.9 (CH), 46.9 (CH$_2$), 36.3 (CH$_2$), 32.2 (CH$_2$), 9.1 (CH$_3$); HRMS (EI) calculated for (C$_{13}$H$_{13}$NOS$_2$) m/z 263.0439, found m/z 263.0443.

Example 4

Chiral Aldol Reactions

The N-propionate derivative 4 was added to cinnamaldehyde to test its diastereoselectivity using the conditions reported by Crimmins, Scheme II. Indeed, when one equivalent of titanium tetrachloride and one equivalent of Hunig's base were employed, a closed transition state where both the aldehyde and the auxiliary are coordinated to the titanium enolate, delivered the "non-Evans" syn aldol product 5. When 2.5 equivalents of (−)-sparteine and one equivalent of titanium tetrachloride were employed, an open transition state where the chiral auxiliary is not coordinated to the titanium enolate, delivered the "Evans" syn aldol product 6. Using the conditions reported by Evans for anti-aldol reaction, catalytic amount of magnesium bromide, trimethylsilyl chloride and triethyl amine, the anti-aldol product 7 was isolated.

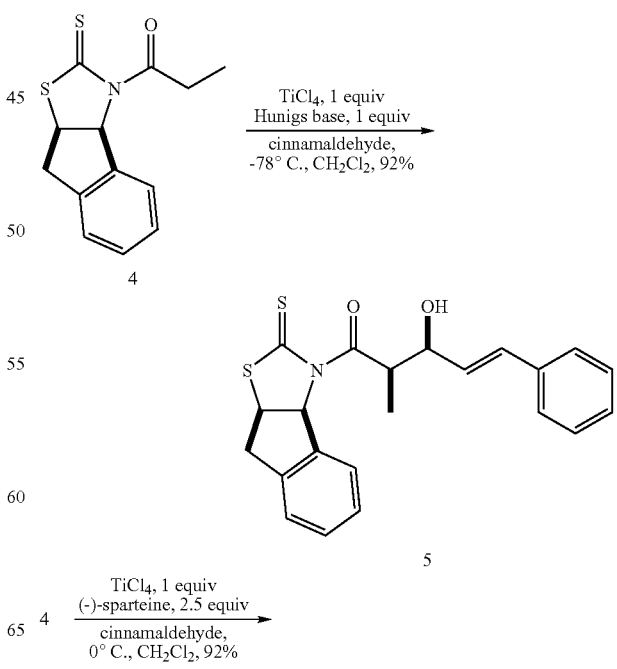

Scheme II

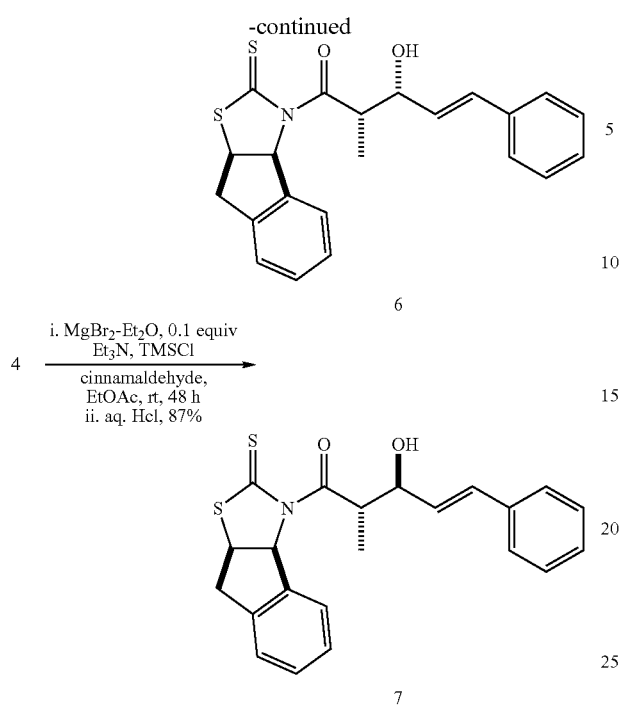

To confirm the relative stereochemistry of the aldol products, compounds 5-7 were reduced with sodium borohydride to the corresponding diols, and treated with 2,2-dimethoxypropane to obtain acetonides 8 and 9. Analysis of the $^1$H-NMR coupling constants of acetonides 8 and 9 was valuable to establish their stereochemistry, Scheme III.

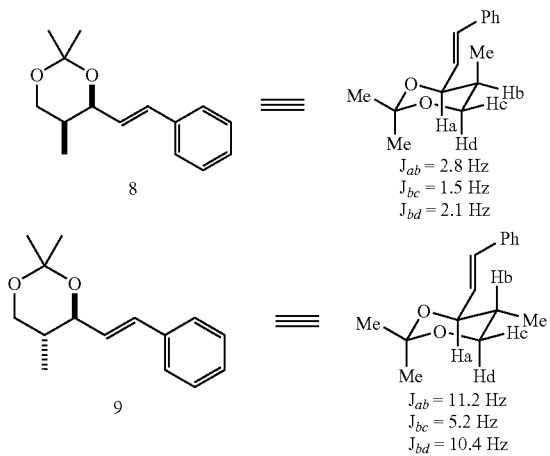

The acetate aldol reaction employing N-acetyl thiazolidinethione 3 was investigated with different types of aldehydes, Table 1. Following the optimized procedure reported by Crimmins, one equivalent of N-acetyl thiazolidinethione 3 was treated with one equivalent of titanium(IV) chloride and one equivalent of (−)-sparteine, and 0.9 equivalents of aldehyde added to the reaction mixture at −78° C. These reaction conditions worked very well with aliphatic, α,β-unsaturated, and aromatic aldehydes. Yields of aldol products ranged between 90 and 98% and diastereoselectivities from 91:9 to 98:2. The stereochemistry of the aldol products was confirmed by X-ray crystallographic analyses of products 10b and 10i. In addition, aldol product 10c was reduced to (+)-(R)-4-methyl-pentane-1,3-diol confirming the stereochemistry of the product.

TABLE 1

Acetate Aldol Reactions of Thiazolidinethione 3

| Entry | Aldehyde | yield (%) | dr (10:11) |
|---|---|---|---|
| 1 | propionaldehyde | 98% | 93:7 |
| 2 | Butyraldehyde | 94% | 93:7 |
| 3 | isobutyraldehyde | 92% | 94:6 |
| 4 | isovaleraldehyde | 97% | 93:7 |
| 5 | Acrolein | 93% | 98:2 |
| 6 | 2-methyl-2-pentenal | 91% | 91:9 |
| 7 | Cinnamaldehyde | 90% | 98:2 |
| 8 | Benzaldehyde | 91% | 93:7 |
| 9 | 3-furaldehyde | 93% | 98:2 |

The versatility of the new chiral auxiliary was investigated by the conversion of the aldol products into other functional groups, Scheme IV. As mentioned previously, aldol product 5 was reduced with sodium borohydride to diol 12. Reduction of the TES protected aldol product 5 with dibal-H delivered aldehyde 13. Hydrolysis of the aldol product 5 with lithium hydroxide gave carboxylic acid 14. Displacement of the thiazolidinethione auxiliary with ethanol and benzyl alcohol mediated by DMAP was carried out smoothly under mild conditions (see, Wu et al., J. Org. Chem. 2004, 69, 6141-6144). Ammonolysis of the chiral auxiliary provide amide 17 (see, Osorio-Lozada et al., Tetrahedron: Asymm. 2004, 15, 3811-3815). As shown with other thiazolidinethiones, the indene-based thiazolidinethione can be easily removed furnishing different functionalities.

Scheme IV

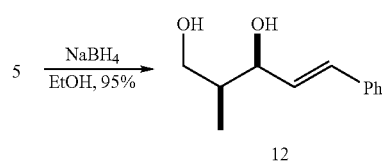

-continued

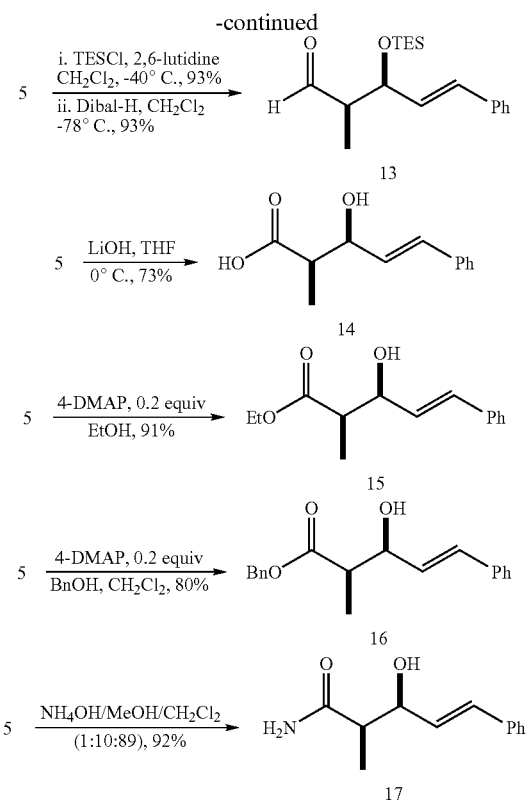

We claim:

1. A method for preparing a compound comprising contacting a compound of formula (I), (I)

wherein
R$^1$-R$^6$ are each independently hydrogen, cyano, halo, nitro, C$_{1-6}$alkyl, C$_{2-6}$alkenyl, C$_{2-6}$alkynyl, C$_{3-8}$cycloalkyl, heterocyclyl, aryl, or heteroaryl, wherein the alkyl, alkenyl, alkynyl, cycloalkyl, heterocyclyl, aryl, and heteroaryl groups are each optionally substituted with one or more groups which are each independently cyano, halo, nitro, C$_{1-6}$alkyl, C$_{2-6}$alkenyl, C$_{2-6}$alkynyl, C$_{3-8}$cycloalkyl, heterocyclyl, aryl, or heteroaryl;
R$^7$ and R$^8$ are each independently hydrogen, C$_{1-6}$alkyl, or phenyl, wherein the alkyl and phenyl groups are each optionally substituted with one or more groups which are each independently halo or C$_{1-6}$alkyl;
or one or more of
(a) R$^1$ and R$^2$ taken together with the carbon atoms to which they are bonded;
(b) R$^2$ and R$^3$ taken together with the carbon atoms to which they are bonded;
(c) R$^3$ and R$^4$ taken together with the carbon atoms to which they are bonded; and
(d) R$^5$ and R$^6$ taken together with the carbon atoms to which they are bonded, form a fused C$_{3-8}$cycloalkyl, heterocyclyl, aryl, or heteroaryl ring wherein the fused ring is optionally substituted with one or more groups which are each independently halo or C$_{1-6}$alkyl;
with sulfuric acid, phosphoric acid, or trifluorosulfonic acid, under suitable reaction conditions to provide a first intermediate; and
contacting the first intermediate with a compound of formula (II), (II)

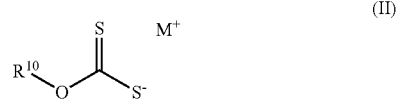

in the presence of an alkali hydroxide, wherein
M$^+$ is lithium, sodium, potassium, or ammonium; and
R$^{10}$ is C$_{1-20}$alkyl, C$_{2-20}$alkenyl, C$_{2-20}$alkynyl, C$_{3-8}$cycloalkylC$_{1-6}$alkyl, heterocyclylC$_{1-6}$alkyl, arylC$_{1-6}$alkyl, heteroarylC$_{1-6}$alkyl, C$_{3-8}$cycloalkyl, heterocyclyl, heteroaryl, or aryl, wherein
R$^{10}$ is optionally substituted with one or more groups which are each independently nitro, cyano, halo, hydroxy, C$_{1-6}$alkoxy, C$_{1-6}$alkyl, or C$_{1-6}$haloalkyl;
under suitable reaction conditions to provide a compound of formula (III), (III)

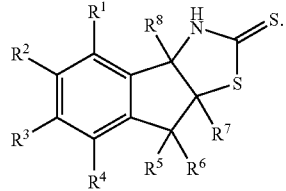

2. The method of claim 1, wherein the compound of formula (I) is of formula (Ia), (Ia)

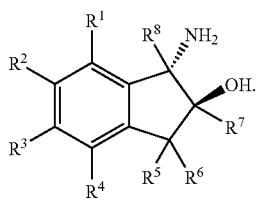

3. The method of claim 1, wherein the compound of formula (I) is of formula (Ib), (Ib)

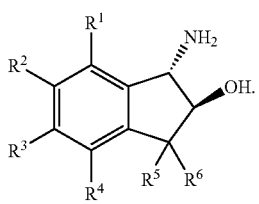

4. The method of claim 1, wherein the compound of formula (I) is of formula (Ic),

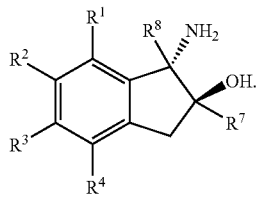

(Ic)

5. The method of claim 1, wherein the compound of formula (I) is of formula (Id),

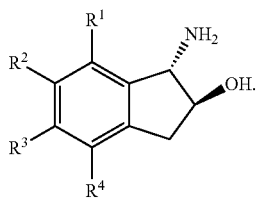

(Id)

6. The method of claim 1, wherein the compound of formula (I) is of formula (Ie),

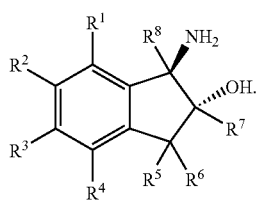

(Ie)

7. The method of claim 1, wherein the compound of formula (I) is of formula (If),

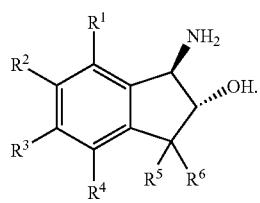

(If)

8. The method of claim 1, wherein the compound of formula (I) is of formula (Ig),

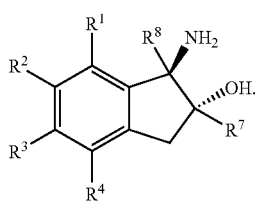

(Ig)

9. The method of claim 1, wherein the compound of formula (I) is of formula (Ih),

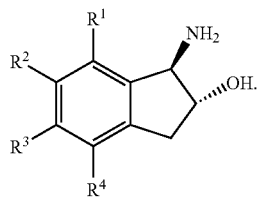

(Ih)

10. The method of claim 1, wherein $R^{10}$ is $C_1$-$C_{20}$ alkyl or phenyl, wherein $R^{10}$ is optionally substituted with one or more groups which are each independently nitro, cyano, halo, hydroxy, $C_{1-6}$alkoxy, $C_{1-6}$alkyl, or $C_{1-6}$haloalkyl.

11. The method of claim 10, wherein $R^{10}$ is $C_{1-20}$alkyl.

12. The method of claim 10, wherein $R^{10}$ is phenyl optionally substituted with one or more groups which are each independently nitro, cyano, halo, hydroxy, $C_{1-6}$alkoxy, $C_{1-6}$alkyl, or $C_{1-6}$haloalkyl.

13. The method of claim 1, wherein the alkali hydroxide is sodium or potassium hydroxide.

14. The method of claims 1, wherein $M^+$ is sodium or potassium.

15. The method of claim 14, wherein $M^+$ is potassium.

16. The method of claim 1, wherein the acid is sulfuric acid.

17. The method of claim 1, further comprising contacting the compound of formula (III) with
(a) a compound of the formula $R^N$—X or $R^N$—O—$R^N$, wherein
X is halo, and
each $R^N$ is independently —C(O)CH($R^{21}$)$R^{20}$ or —C(O)C($R^{21}$)=CH($R^{20}$), wherein $R^{20}$ is hydrogen, $C_{1-6}$alkyl, $C_{2-6}$alkenyl, $C_{2-6}$alkynyl, aryl$C_{1-6}$alkyl, aryl $C_{2-6}$alkenyl, heteroaryl$C_{1-6}$alkyl, heteroaryl$C_{2-6}$alkenyl, $C_{3-8}$cycloalkyl$C_{1-6}$alkyl, $C_{3-8}$cycloalkyl$C_{2-6}$alkenyl heterocyclyl$C_{1-6}$alkyl, heterocyclyl$C_{2-6}$alkenyl, aryl, heteroaryl, $C_{3-8}$cycloalkyl, or heterocyclyl; and $R^{21}$ is hydrogen or $C_{1-6}$alkyl;
or
(b) a compound of the formula $R^N$—OH in the presence of an amide coupling reagent, under suitable reaction conditions to provide a compound of formula (IV),

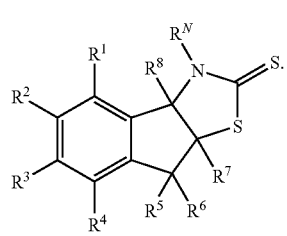

(IV)

18. The method of claim 17, wherein $R^N$ is —C(O)$C_{1-6}$alkyl or —C(O)C($R^{21}$)=CH($R^{20}$),
wherein $R^{20}$ and $R^{21}$ are independently hydrogen or $C_{1-6}$alkyl.

19. The method of claim 17, comprising contacting the compound of formula (III) with a compound of the formula $R^N$—X.

20. The method of claim 17, comprising contacting the compound of formula (III) with a compound of the formula $R^N$—O—$R^N$.

21. The method of claim 17, comprising contacting the compound of formula (III) with a compound of the formula $R^N$—OH and an amide coupling agent.

22. The method of claim 21, wherein the amide coupling agent is a carbodiimide, a N,N'-carbonyldiimizadole, or a benzotriazol-1-yloxyphosphonium salt.

23. A method for preparing a compound comprising contacting a compound of formula (I),

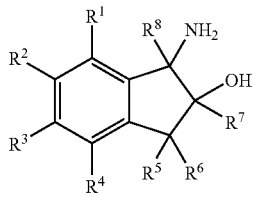

(I)

wherein
$R^1$-$R^6$ are each independently hydrogen, cyano, halo, nitro, $C_{1-6}$alkyl, $C_{2-6}$alkenyl, $C_{1-6}$alkynyl, $C_{3-8}$cycloalkyl, heterocyclyl, aryl, or heteroaryl, wherein the alkyl, alkenyl, alkynyl, cycloalkyl, heterocyclyl, aryl, and heteroaryl groups are each optionally substituted with one or more groups which are each independently cyano, halo, nitro, $C_{1-6}$alkyl, $C_{2-6}$alkenyl, $C_{2-6}$alkynyl, $C_{3-8}$cycloalkyl, heterocyclyl, aryl, or heteroaryl;

$R^7$ and $R^8$ are each independently hydrogen, $C_{1-6}$alkyl, or phenyl, wherein the alkyl and phenyl groups are each optionally substituted with one or more groups which are each independently halo or $C_{1-6}$alkyl;

or one or more of
(a) $R^1$ and $R^2$ taken together with the carbon atoms to which they are bonded;
(b) $R^2$ and $R^3$ taken together with the carbon atoms to which they are bonded;
(c) $R^3$ and $R^4$ taken together with the carbon atoms to which they are bonded; and
(d) $R^5$ and $R^6$ taken together with the carbon atoms to which they are bonded, form a fused $C_{3-8}$cycloalkyl, heterocyclyl, aryl, or heteroaryl ring wherein the fused ring is optionally substituted with one or more groups which are each independently halo or $C_{1-6}$alkyl;

with either
(i) sulfuric acid under suitable reaction conditions to provide a compound of the formula,

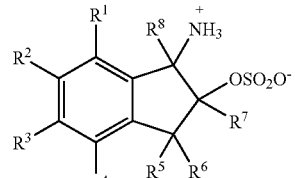

(VI)

(ii) trifluoromethylsulfonic acid under suitable reaction conditions to provide a compound of the formula,

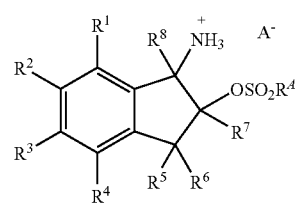

(V)

wherein $R^A$ is —$CF_3$ and $A^-$ is $R^A SO_2 O^-$; or
(iii) phosphoric acid under suitable reaction conditions to provide a compound of the formula,

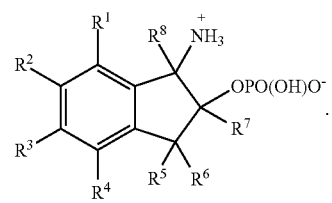

(VII)

24. The method of claim 23, wherein the acid is sulfuric acid.

* * * * *